United States Patent
Gouko et al.

(10) Patent No.: US 10,197,376 B2
(45) Date of Patent: *Feb. 5, 2019

(54) RUNOUT DETECTION DEVICE CONFIGURED TO DETECT RUNOUT OF THE ROTATING MEMBER BASED ON THE HEAT FLUX DETECTED BY THE HEAT

(71) Applicant: DENSO CORPORATION, Kariya, Aichi-pref. (JP)

(72) Inventors: Norio Gouko, Kariya (JP); Toshihisa Taniguchi, Kariya (JP); Atusi Sakaida, Kariya (JP); Keiji Okamoto, Kariya (JP); Yoshihiko Shiraishi, Kariya (JP); Masahiro Asano, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/667,768

(22) Filed: Aug. 3, 2017

(65) Prior Publication Data

US 2018/0038678 A1 Feb. 8, 2018

(30) Foreign Application Priority Data

Aug. 4, 2016 (JP) .................................. 2016-153920

(51) Int. Cl.
| | | |
|---|---|---|
| *G01L 5/06* | (2006.01) | |
| *G01B 5/30* | (2006.01) | |
| *F01D 17/08* | (2006.01) | |
| *G01B 5/00* | (2006.01) | |

(Continued)

(52) U.S. Cl.
CPC .............. *G01B 5/30* (2013.01); *F01D 17/085* (2013.01); *G01B 5/0004* (2013.01); *G01B 5/252* (2013.01); *G01N 25/20* (2013.01)

(58) Field of Classification Search
CPC ... G01L 5/06; G01L 5/04; G01L 5/045; G01L 5/106; G01K 17/00; G01N 25/00; G01N 25/20; G01B 21/32; B65G 43/00
See application file for complete search history.

(56) References Cited

U.S. PATENT DOCUMENTS 4,674,310 A * 6/1987 Ginzburg ................ B21B 38/02
    72/11.4
2008/0307885 A1* 12/2008 Ravitch .................... G01H 5/00
    73/597

(Continued)

FOREIGN PATENT DOCUMENTS

JP    H06235422 A    8/1994

*Primary Examiner* — Lisa Caputo
*Assistant Examiner* — Brandi Hopkins
(74) *Attorney, Agent, or Firm* — Harness, Dickey & Pierce. P.L.C.

(57) ABSTRACT

In a runout detection device for detecting runout of a rotating member, a displacement unit abuts on the rotating member, and is displaced in accordance with displacement of the rotating member while the rotor abuts on the displacement unit. An elastic member elastically deforms in accordance with displacement of the displacement unit. A heat flux sensor detects a heat flux generated by elastic deformation of the elastic member. The runout detection device is configured to detect runout of the rotating member based on the heat flux detected by the heat flux sensor.

6 Claims, 9 Drawing Sheets

(51) Int. Cl.
*G01N 25/20* (2006.01)
*G01B 5/252* (2006.01)

(56) References Cited

U.S. PATENT DOCUMENTS

2017/0299383 A1* 10/2017 Gouko .................. G01B 21/32
2017/0299451 A1* 10/2017 Gouko .................. G01N 25/00

* cited by examiner

RUNOUT DETECTION DEVICE CONFIGURED TO DETECT RUNOUT OF THE ROTATING MEMBER BASED ON THE HEAT FLUX DETECTED BY THE HEAT

CROSS-REFERENCE TO RELATED APPLICATION

This application is based on and claims the benefit of priority from earlier Japanese Patent Application No. 2016-153920 filed Aug. 4, 2016, the description of which is incorporated herein by reference.

BACKGROUND OF THE INVENTION

Technical Field of the Invention

The present invention relates to runout detection devices, each of which detects runout of a rotating body, i.e. a rotor.

Related Art

Conventionally, techniques for detecting runout of a rotating body, specifically, techniques for detecting axial runout of a rotating body that is rotating, have been known. For example, an increase in the axial runout of a rotary processing tool, such as a molding roller, causes a problem, such as an abnormality in the shape of an object, processed by the processing tool. Thus, conventional techniques for example detect the axial runout of the processing tool that is rotating, and control the processing tool while the axial runout is maintained within a limited range.

As a device related to this type of techniques, a runout correction device is proposed by Japanese Patent Application Publication No. H06-235422 (Patent Literature 1), for example.

This runout correction device includes: a reference ring which serves as a reference for detecting runout of a rotating body which is a measurement target; three proximity sensors which detect runout of the reference ring, that is, runout of the rotating body; and a piezo actuator which corrects the position of the rotating body.

Specifically, the reference ring is in the shape of a circular cylinder having two circular surfaces. The reference ring is secured to an end portion of the rotating body such that the center of one of the two circular surfaces coincides with the center of gravity of the rotating body. The three proximity sensors are each disposed at a predetermined distance from the side surface of the cylindrical reference ring in its radial direction. The positions of the three proximity sensors in the circumferential direction of the cylindrical reference ring are different from each other.

The runout correction device detects the degree of runout of the rotating body on the basis of changes in values measured by the respective proximity sensors; the changes of the measured values depend on displacement of the rotating body. Then, the runout correction device controls, based on the detected degree of the runout of the rotating body, the piezo actuator to thereby correct the position of the rotating body such that the rotating body is located at a proper position.

Specifically, the runout correction device obtains the trajectory of the runout of the axis of the rotating body based on the pieces of measurement data measured by the three proximity sensors. Then, the runout correction device corrects the runout of the rotating body based on the trajectory of the runout of the rotating body.

The proximity sensors in the runout correction device disclosed in Patent Literature 1 replace, for example, movement information and presence information of the reference ring serving as a detection target with electrical signals. Known examples of such a method of replacing these items of information with electrical signals generally include 1. A method of detecting a change in electric capacitance due to proximity of a detection target
2. A method of using an eddy current produced by electromagnetic induction in a metal body as a detection target Such a proximity sensor detects, as runout of the rotating body, a value corresponding to the distance of a part of the reference ring, which passes by the proximity sensor, from the center of the reference ring.

SUMMARY

The device disclosed in Patent Literature 1 detects runout of a reference ring using proximity sensors. Specifically, each proximity sensor detects, as runout of the rotating body, a value corresponding to the distance of a part of the reference ring, which passes by the proximity sensor, from the center of the reference ring. Unfortunately, such a proximity sensor may have an insufficient accuracy of detecting runout of a rotating body, because the proximity sensor does not directly detect change of the reference ring as a detection target. In particular, such a proximity sensor may have worse detection accuracy if a detection target has a complex shape, such as a curved surface like the Patent Literature 1 as compared with a detection accuracy obtained by the proximity sensor if a detection target has a simply planar shape and maintains a substantially constant distance from the proximity sensor.

In view of the aforementioned circumstances, a first aspect of the present disclosure seeks to provide runout detection devices, each of which is capable of addressing the problem set forth above.

Specifically, a second aspect of the present disclosure seeks to provide such devices, each of which is capable of detecting runout of a rotating member with higher accuracy.

According to an exemplary aspect of the present disclosure, there is provided a runout detection device for detecting runout of a rotating member. The runout detection device includes a displacement unit that abuts on the rotating member, and is displaced in accordance with displacement of the rotating member while the rotating member abuts on the displacement unit. The runout detection device includes an elastic member that elastically deforms in accordance with displacement of the displacement unit, and a heat flux sensor that detects a heat flux generated by elastic deformation of the elastic member. The runout detection device is configured to detect runout of the rotating member based on the heat flux detected by the heat flux sensor.

In the runout detection device, the displacement unit is displaced in accordance with runout or a change in runout of the rotating member, and the elastic member deforms in accordance with this displacement of the displacement unit. The heat flux sensor detects a heat flux due to this deformation of the elastic member. This enables the runout detection device to detect runout or a change in runout of the rotating member. In particular, the runout detection device is capable of directly measuring runout of the rotating member, that is, displacement of the rotating member. This therefore enables the runout detection device to accurately detect runout of the rotating member compared to, for example, the runout correction device disclosed in the published patent document described above.

BRIEF DESCRIPTION OF THE DRAWINGS

Other aspects of the present disclosure will become apparent from the following description of an embodiment with reference to the accompanying drawings in which.

DETAILED DESCRIPTION OF EMBODIMENTS

Figure 1:
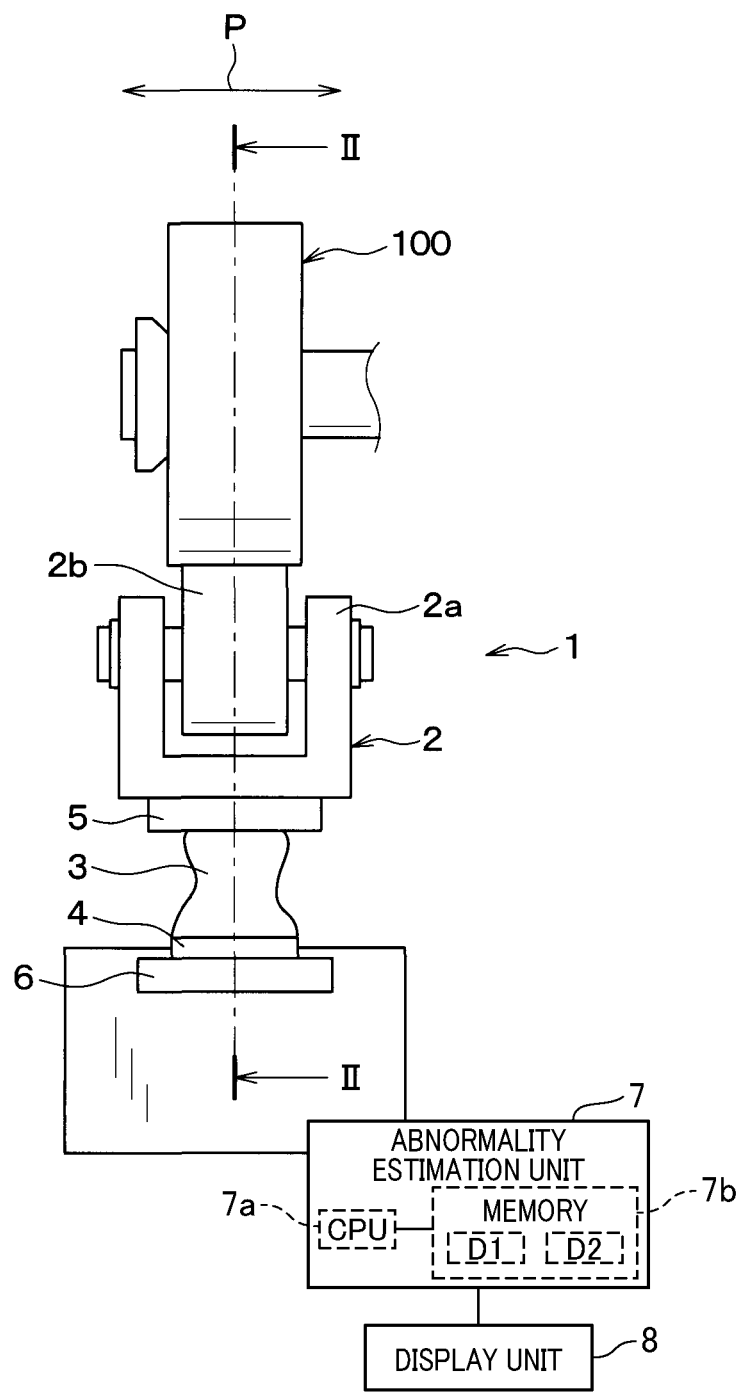
FIG. 1 is a view illustrating an overall configuration in which a runout detection device according to the first embodiment is installed for a rotating body.

The following describes embodiments of the present disclosure with reference to the drawings. In the embodiments, like parts between the embodiments, to which like reference characters are assigned, are omitted or simplified to avoid redundant description.

First Embodiment

Figure 2:
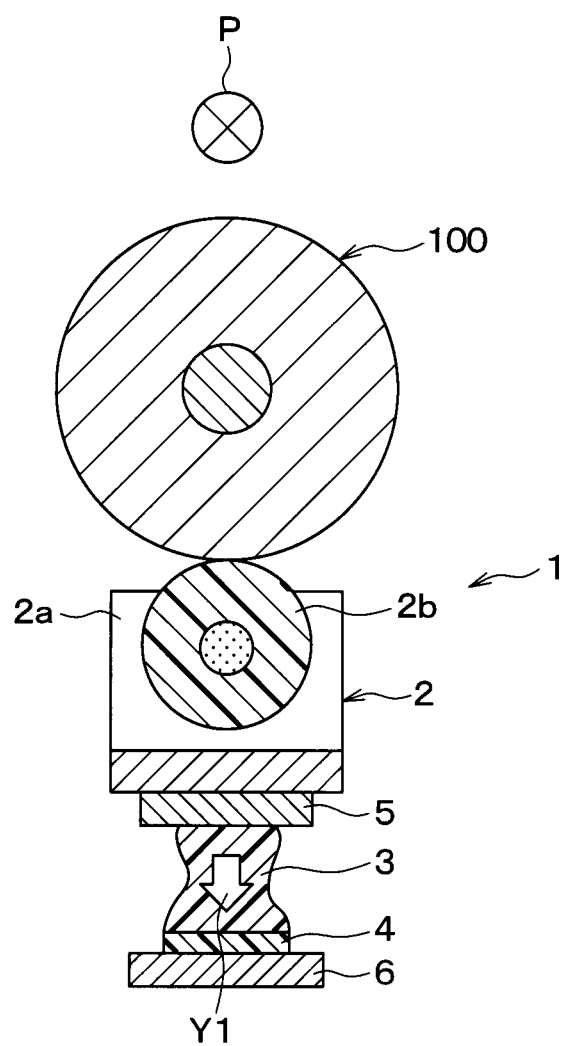
FIG. 2 is a view illustrating a configuration of the runout detection device illustrated in FIG. 1, at a cross-section taken along line II-II of FIG. 1.
Figure 3:
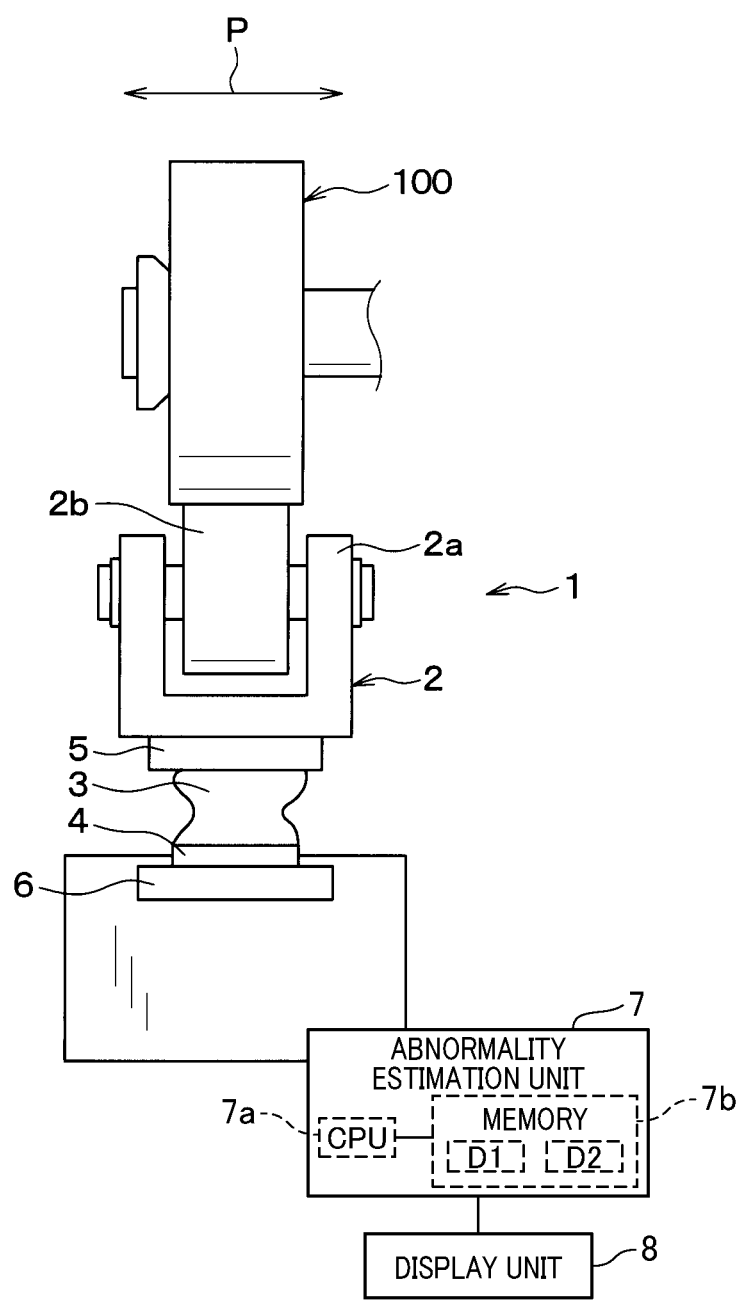
FIG. 3 is another view illustrating the overall configuration for the runout detection device illustrated in FIG. 1.

The following describes a runout detection device 1 according to the first embodiment of the present disclosure with reference to FIG. 1 to FIG. 6. As illustrated in FIG. 1 and FIG. 2, the runout detection device 1 abuts on a rotating member 100 and detects runout (that is, the degree of runout) of the rotating member 100 or a change in the runout during rotation of the rotating member 100. The rotating member 100 is, for example, a spindle which turns a molding roller, a cutting tool, or the like. Note that FIG. 1 and FIG. 2 are views illustrating an overall configuration for the runout detection device 1 at the start of measurement, and FIG. 3 is a view illustrating an overall configuration for the runout detection device 1 when the runout of the rotating member 100 increases. The arrows denoted by a reference sign P in FIG. 1 to FIG. 3 represent the direction of the axis of rotation of the rotating member 100. The arrow denoted by a reference sign Y1 in FIG. 2 represents the direction in which an elastic member 3 deforms when the runout of the rotating member 100 increases from that at the start of the measurement.

As illustrated in FIG. 1, the runout detection device 1 according to the present embodiment includes a displacement unit 2, the elastic member 3, a heat flux sensor 4, a plate member 5, a plate member 6, an abnormality estimation unit 7, and a display unit 8. As illustrated in FIG. 1 and FIG. 2, the runout detection device 1 has a configuration in which the plate member 6, the heat flux sensor 4, the elastic member 3, the plate member 5, and the displacement unit 2 are stacked in this order from the bottom. The direction in which the components 6, 4, 3, 5, and 2 are stacked will be referred to as a stack direction.

The displacement unit 2 is a member having a part that is brought into contact with the rotating member 100 so as to receive a load due to runout of the rotating member 100. The displacement unit 2 is displaced in accordance with displacement of the rotating member 100 when the displacement unit 2 is in contact with the rotating member 100. As illustrated in FIG. 1 and FIG. 2, the displacement unit 2 according to the present embodiment includes a base portion 2a and a roller portion 2b.

The base portion 2a of the displacement unit 2 is directly or indirectly connected to the elastic member 3 to apply, to the elastic member 3, pressing force corresponding to the runout of the rotating member 100. Here, the base portion 2a of the displacement unit 2 is configured, as an example, to include a bottom plate portion including a plate member and two side wall portions extending in substantially the same direction from both ends of the bottom plate portion, as illustrated in FIG. 1 and FIG. 2. In other words, this base portion 2a is shaped so that a cross-section thereof has a U-shape. The bottom plate portion of the base portion 2a is connected to the elastic member 3 via the plate member 5. The base portion 2a of the displacement unit 2 includes a material such as stainless steel, for example. The plate member 5 includes a material such as stainless steel, for example.

As illustrated in FIG. 1 and FIG. 2, the roller portion 2b is a circular cylindrical rotating member rotatably supported by the base portion 2a. Specifically, the roller portion 2b is disposed between the two side wall portions of the basic portion 2a and rotatably supported by each of the two side wall portions. The roller portion 2b rotates following rotation of the rotating member 100 when the roller portion 2b is in contact with the rotating member 100. The roller portion 2b includes a resin such as urethane or Delrin®, for example.

The base portion 2a and the roller portion 2b are displaced in accordance with displacement of the rotating member 100. Specifically, in the present embodiment, the roller portion 2b receives a load due to the runout of the rotating member 100, resulting in the base portion 2a together with the roller portion 2b being displaced in a direction intersecting the direction of an axis of rotation P of the rotating member 100. Furthermore, such displacement of the base portion 2a results in pressing force being applied to the elastic member 3 via the plate member 5, causing deformation of the elastic member 3.

The elastic member 3 is a member that elastically deforms in accordance with displacement of the displacement unit 2. Specifically, when the displacement unit 2 is displaced in accordance with runout of the rotating member 100, the elastic member 3 deforms in accordance with the displacement of the displacement unit 2. The elastic member 3 includes a resin such as urethane, for example. The elastic member 3 includes a material having an elastic modulus lower than that of the displacement unit 2. Note that the elastic member 3 may include a material having an elastic modulus higher than that of the displacement unit 2. As illustrated in FIG. 1 and FIG. 2, the elastic member 3 has opposing first and second ends in the stack direction. The elastic member 3 is in contact with the plate member 5 at the first end and is in contact with the heat flux sensor 4 at the second end.

The heat flux sensor 4 is a sensor that detects a heat flux due to elastic deformation of the elastic member 3. As illustrated in FIG. 1 and FIG. 2, the heat flux sensor 4 is disposed in a position that allows detection of the heat flux generated by elastic deformation of the elastic member 3. Specifically, the heat flux sensor 4 is in contact with the elastic member 3. Furthermore, the heat flux sensor 4 outputs a sensor signal corresponding to the heat flux that travels outward from the inside of the elastic member 3.

In the present embodiment, the heat flux sensor 4 having the following configuration is used as an example. Specifically, as illustrated in FIG. 4 and FIG. 5, the heat flux sensor 4 has a structure in which an insulating base 40, a front protective member 41, and a back protective member 42 are integrally formed while first interlayer connection members 43 and second interlayer connection members 44 are alternately connected in series inside this integrated unit.

Figure 4:
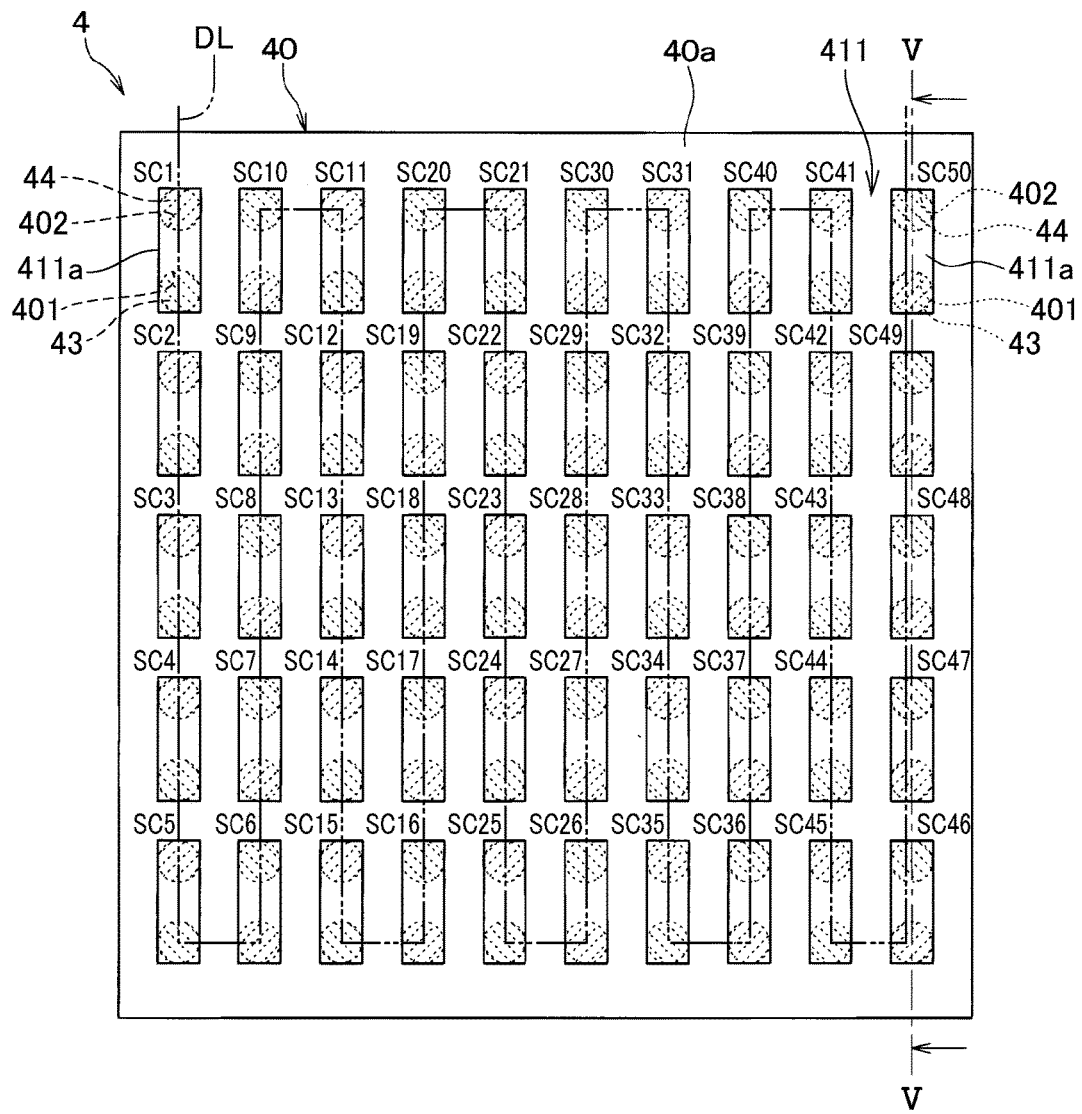
FIG. 4 is a plan view illustrating a heat flux sensor included in the runout detection device illustrated in FIG. 1.
Figure 5:
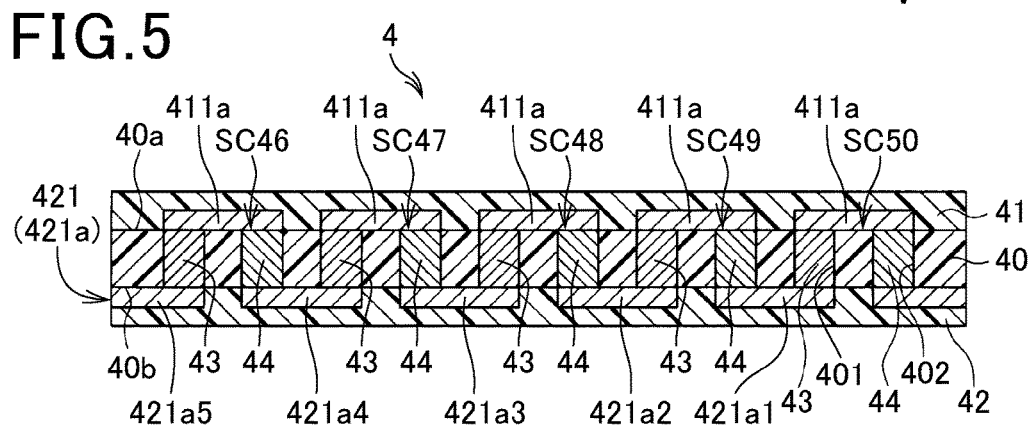
FIG. 5 is a view illustrating a cross-section of the heat flux sensor illustrated in FIG. 4, taken along line V-V of FIG. 4.

Note that an illustration of the front protective member 41 is omitted in FIG. 4. Each of the insulating base 40, the front protective member 41, and the back protective member 42 is formed into a film by using a flexible resin material (for example, a thermoplastic resin).

The insulating base 40 has a rectangular plate-like shape with a first end 40E and a second end 40E2 in its longitudinal direction (see FIG. 4A). The insulting base 40 has plural pairs of first via holes 401 and second via holes 402 penetrating the insulating base 40 in the thickness direction thereof. Each of the first via hole 401 is filled with a corresponding one of the first interlayer connection members 43; each of the first interlayer connection members 43, which has opposing first and second ends, is composed of a thermoelectric material (for example, a metal or a semiconductor). Each of the second via holes 402 is filled with a corresponding one of the second interlayer connection members 44; each of the second interlayer connection members 44, which has opposing first and second ends, is composed of a thermoelectric material (for example, a metal or a semiconductor) different from that of the first interlayer connection member 43.

As illustrated in FIG. 4, the plural pairs of first via holes 401 and second via holes 402 are arranged in a matrix.

Referring to FIG. 4, a front conductor pattern 411, which is comprised of front conductor segments 411a, is disposed on a front surface 40a of the insulating base 40. The front conductor segments 411a, each having a rectangular shape, are arranged in a matrix such that each of the conductor segments 411a faces a corresponding one of the pairs of the first and second via holes 401 and 402. This front conductor pattern 411 serves as a connection unit.

Specifically, the first end of the first interlayer connection member 43 and the first end of the second interlayer connection member 44 filled in the respective first and second via holes 401 and 402 of each pair are connected to one another via a corresponding one of the front conductor elements 411a to constitute a series-connected thermocouple member SC. That is, as illustrated in FIG. 4, the heat flux sensor 4 includes fifty series-connection thermocouple members SC1 to SC50.

A back conductor pattern 421, which is comprised of back conductor segments 421a, is disposed on a back surface 40b of the insulating base 40. The back conductor segments 421a, each having a rectangular shape, are arranged to enable the thermocouple members SC1 to SC50 to be connected in series to each other.

Specifically, as illustrated in FIG. 5, the second end of the first interlayer connection member 43 of the thermocouple member SC50 is connected to a corresponding one of the back conductor segments 421a, which will be referred to as a back conductor segment 421a1. The second end of the second interlayer connection member 44 of the thermocouple member SC49 is connected to the same back conductor segment 421a1. Similarly, the second end of the first interlayer connection member 43 of the thermocouple member SC49 is connected to a corresponding one of the back conductor segments 421a, which will be referred to as a back conductor segment 421a2. The second end of the second interlayer connection member 44 of the thermocouple member SC48 is connected to the same back conductor segment 421a2.

In addition, the second end of the first interlayer connection member 43 of the thermocouple member SC48 is connected to a corresponding one of the back conductor segments 421a, which will be referred to as a back conductor segment 421a3. The second end of the second interlayer connection member 44 of the thermocouple member SC47 is connected to the same back conductor segment 421a3. Similarly, the second end of the first interlayer connection member 43 of the thermocouple member SC47 is connected to a corresponding one of the back conductor segments 421a, which will be referred to as a back conductor segment 421a4. The second end of the second interlayer connection member 44 of the thermocouple member SC46 is connected to the same back conductor segment 421a4. The second end of the first interlayer connection member 43 of the thermocouple member SC46 is connected to a corresponding one of the back conductor segments 421a, which will be referred to as a back conductor segment 421a5.

That is, the back conductor segments 421a1 to 421a5 enable the thermocouple members SC46 to SC50 to be connected in series to each other.

Note that hereinafter, the first ends of the first and second interlayer connection members 43 and 44 on which the front protective member 41 is located will be referred to as a front side of the heat flux sensor 4. Likewise, the second ends of the first and second interlayer connection members 43 and 44 on which the back protective member 42 is located will be referred to a back side of the heat flux sensor 4.

Specifically, the back conductor segments 421a enables the thermocouple members SC1 to SC50 to be connected in series from the thermocouple member SC1 to the thermocouple member SC50 in this order along a chain double-dashed line DL as illustrated in FIG. 4. In other words, the heat flux sensor 4 is comprised of the thermocouple members SC1 to SC50 that are series connected from the thermocouple member SC1 to the thermocouple member SC50 between the front side of the heat flux sensor 4 and the back side of the heat flux sensor 4.

As illustrated in FIG. 1 and FIG. 2, in the present embodiment, the heat flux sensor 4 configured in the aforementioned manner is disposed so that the elastic member 3 is located on the front side of the heat flux sensor 4. Note that the heat flux sensor 4 stays secured to the plate member 6 disposed on the back side of the heat flux sensor 4.

In the present embodiment, passage of a heat flux through the heat flux sensor 4 in the thickness direction of the heat flux sensor 4 creates a difference in temperature between the front side and the back side of the heat flux sensor 4. Specifically, passage of a heat flux through the heat flux sensor 4 in the thickness direction of the heat flux sensor 4 creates a difference in temperature, which is detected by each of the thermocouple members SC1 to SC50, between the front conductor pattern 411 disposed on the front side of the heat flux sensor 4 and the back conductor pattern 421 disposed on the back side of the heat flux sensor 4. As a result, electromotive force is generated by the series-connected thermocouple members SC1 to SC50 in accordance with the Seebeck effect. Then, the heat flux sensor 4 outputs, as a sensor signal, the electromotive force (for example, voltage) generated by the series-connected thermocouple members SC1 to SC50; the intensity of the sensor signal depends on the heat flux flowing between the front side and the back side of the heat flux sensor 4. Note that the heat flux sensor 4 in the present embodiment is configured, as an example, to generate a positive electromotive force when heat flux flows from the front side to the back side of the heat flux sensor 4.

The elastic member 3 generates hot energy inside thereof upon being compressed or expanded, and generates cold energy inside thereof upon being restored from the compressed state with external force acting thereon to the natural state by elastic deformation resulting from a release of compression. The absolute value of the electromotive force generated by the heat flux sensor 4 and the deformation (for example, an amount of deformation or an amount of change in the amount of deformation) of the elastic member 3 correlate with each other. In other words, for example, basically, as the amount of deformation of the elastic member 3 increases, the heat flux that is generated by the deformation of the elastic member 3 increases, and the difference in temperature between the front side and the back side of the heat flux sensor 4 increases. Therefore, basically, as the amount of deformation of the elastic member 3 increases, the difference in temperature between the front conductor pattern 411 disposed on the front side of the heat flux sensor 4 and the back conductor pattern 421 disposed on the back side of the heat flux sensor 4 increases, and the absolute value of the electromotive force that is generated by the heat flux sensor 4 increases.

The heat flux sensor 4 in the present embodiment is configured as described above and therefore can be disposed even on a surface other than a simple flat surface (such as a curved surface), for example, in a flexible way. In addition, this heat flux sensor 4 has the advantage that since the thickness of the heat flux sensor 4 can be reduced with the output of sufficient electromotive force made available, a reduction in the thickness of the heat flux sensor 4 reduces the thermal resistance inside of the heat flux sensor 4 so that errors in detection can be reduced.

The abnormality estimation unit 7 is connected to the heat flux sensor 4, so that the abnormality estimation unit 7 receives the sensor signal output from the heat flux sensor 4. The abnormality estimation unit 7 detects, based on the received sensor signal, runout (that is, the degree of runout) of the rotating member 100 on the basis of the heat flux generated by elastic deformation of the elastic member 3 and detected by the heat flux sensor 4. Specifically, when the result of detection by the heat flux sensor 4 has a value exceeding a predetermined threshold value t, the abnormality estimation unit 7 estimates that the rotating member 100 is abnormally run out, i.e. abnormally deviated.

The abnormality estimation unit 7 is designed as an electronic control unit as an example, which is comprised of, for example, a microcomputer 7a, a memory 7b serving as a storage unit, and peripheral units. The memory 7b stores data D1 related to the relationship between positions of the rotating member 100) and electromotive force caused to be generated by the heat flux sensor 4 when the plate member 6 is placed in a predetermined position. Furthermore, the memory stores data D2 related to the association between changes in the runout of the rotating member 100 and electromotive force caused to be generated by the heat flux sensor 4. Note that the memory 7b includes, for example, a non-transitory computer-readable storage medium.

Furthermore, the abnormality estimation unit 7 controls the operation of the display unit 8 by performing a predetermined abnormality estimation process according to a preset program. Under the control of the abnormality estimation unit 7, the display unit 8 is then caused to display the result of the abnormality estimation process.

Next, an operation of the runout detection device 1 according to the present embodiment will be described.

As illustrated in FIG. 1 and FIG. 2, the plate member 6 of the runout detection device 1 is disposed in the aforementioned predetermined position, and the rotating member 100 abuts on the displacement unit 2 of the runout detection device 1. At this time, depending on the position of the displacement unit 2 of the runout detection device 1 and the position, runout, etc., of the rotating member 100, the elastic member 3 is compressed to some extent as a result of displacement of the displacement unit 2. This is the state of the runout detection device 1 at the start of measurement in the present embodiment.

At the start of measurement, first, the elastic member 3 is compressed as described above, and thus molecules of irregular geometry within the elastic member 3 are aligned, causing hot energy to be generated inside of the elastic member 3. As a result, a heat flux flowing from the inside to the outside of the elastic member 3 is generated, and the flow of this heat flux from the front side to the back side of the heat flux sensor 4 creates a difference in temperature between the front side and the back side of the heat flux sensor 4. Subsequently, electromotive force in the form of a sensor signal corresponding to the position of the rotating member 100 is generated in the heat flux sensor 4. At this time, on the basis of this electromotive force, the abnormality estimation unit 7 calculates the position of the rotating member 100 at the start of measurement. Specifically, the abnormality estimation unit 7 reads the above-described data D1 stored in the memory 7b, and calculates the position of the rotating member 100 on the basis of the read data D1. Then, the abnormality estimation unit 7 stores this position of the rotating member 100 into the memory as the position of the rotating member 100 at the start of measurement (hereinafter referred to as an initial position). Note that in the present embodiment, the heat flux generated by compression of the elastic member 3 at the start of measurement is originally small in amount and released outward with time, decreasing to such a small amount that it is not detected by the heat flux sensor 4 after a predetermined time elapses.

When the rotating member 100 is largely deviated, i.e. run out, after the start of measurement, the displacement unit 2 is displaced downward as viewed in FIG. 3, and thus the elastic member 3 is more compressed than that at the start of measurement, as illustrated in FIG. 3. Accordingly, electromotive force corresponding to the degree of the runout of the rotating member 100 is generated in the heat flux sensor 4, and is detected by the abnormality estimation unit 7 as runout of the rotating member 100, specifically, radial runout of the rotating member 100 that causes the rotating member 100 to be displaced toward the displacement unit 2. At this time, on the basis of this runout of the rotating member 100 and the aforementioned initial position, the abnormality estimation unit 7 calculates the current position of the rotating member 100 (hereinafter referred to as a second position).

When there occurs runout that causes the rotating member 100 to be displaced away from the displacement unit 2, the displacement unit 2 is displaced upward as viewed in FIG. 3 so as to return to the state at the start of measurement. This releases the compression of the elastic member 3 in the compressed state (for example, the state at the start of measurement or the state in which the elastic member 3 is more compressed than that at the start of measurement), allowing the elastic member 3 to be restored by elastic deformation, which results in cold energy, i.e. temperature reduction, being generated inside of the elastic member 3. Accordingly, the temperature of the front side of the heat flux sensor 4 is reduced and as a result, the difference in temperature between the front side and the back side of the heat flux sensor 4 is different from that at the start of measurement. This leads to a change in the electromotive force that is generated in the heat flux sensor 4, and the abnormality estimation unit 7 detects this change as runout that causes the rotating member 100 to be displaced away from the displacement unit 2. At this time, on the basis of this runout of the rotating member 100 and the aforementioned second position, the abnormality estimation unit 7 calculates the current position of the rotating member 100. Note that in the case where the difference in temperature between the front side and the back side of the heat flux sensor 4 is reversed in sign between before and after displacement of the rotating member 100, the sign of the value of the electromotive force is also reversed. Subsequently, on the basis of the detected runout or change in runout of the rotating member 100, the abnormality estimation unit 7 performs abnormality estimation of whether the runout of the rotating member 100 is abnormal, and causes the display unit 8 to display the result of the abnormality estimation.

As described above, the runout detection device 1 is configured such that

1. The displacement unit 2 is displaced in accordance with runout or a change in runout of the rotating member 100
2. The elastic member 3 deforms in accordance with this displacement of the displacement unit 2
3. The heat flux sensor 4 detects a change in the heat flux due to the deformation of the elastic member 3

This therefore enablers the runout detection device 1 to detect, based on the detected change of the heat flux, runout or a change in runout of the rotating member 100, and to determine whether the runout of the rotating member 100 is abnormal on the basis of the detected runout or change in runout of the rotating member 100. In particular, the runout detection device 1 is capable of directly measuring runout of the rotating member 100, that is, displacement of the rotating member 100. This enables the runout detection device 1 to detect runout of the rotating member 100 with higher accuracy as compared to, for example, the runout correction device disclosed in the published patent document described above.

Figure 6:
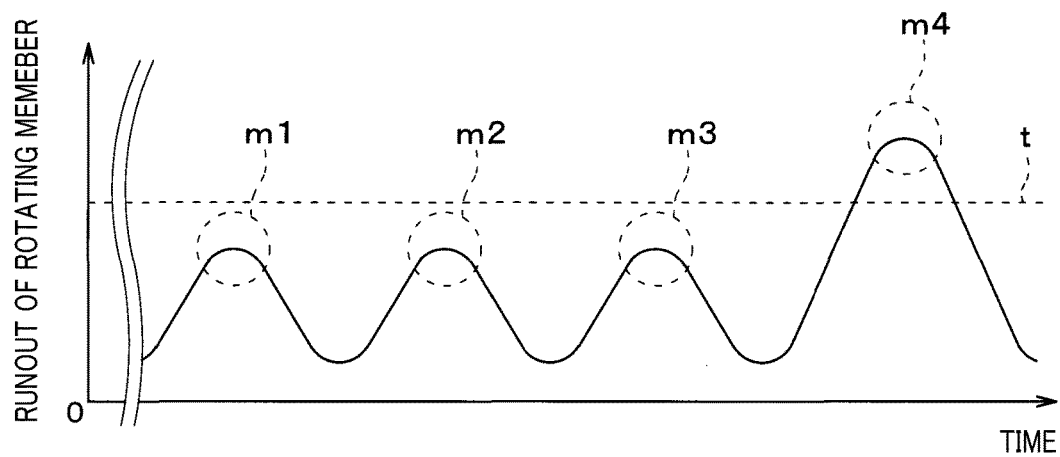
FIG. 6 is a view illustrating one example of runout transition of the rotating member during an operation of the runout detection device illustrated in FIG. 1.

FIG. 6 shows the transition of the runout of the rotating member 100 with time plotted on the horizontal axis and values of the runout of the rotating member 100 plotted on the vertical axis. Note that the line denoted by a reference sign t in FIG. 6 represents a threshold value as a boundary between normal and abnormal runouts of the rotating member 100. For example, in the case where the runout of the rotating member 100 transitions as in FIG. 6, when the runout of the rotating member 100 exceeds a threshold value t such as m4, the abnormality estimation unit 7 estimates that the rotating member 100 is extremely largely deviated, i.e. run out. Subsequently, this information is displayed on the display unit 8.

As described above, the runout detection device 1 includes: the displacement unit 2 which is displaced in accordance with runout or a change in runout of the rotating member 100 when the displacement unit 2 is in contact with the rotating member 100; and the elastic member 3 which elastically deforms in accordance with displacement of the displacement unit 2. In addition, the runout detection device 1 includes the heat flux sensor 4 which detects a heat flux generated by elastic deformation of the elastic member 3. Furthermore, the runout detection device 1 detects runout of the rotating member 100 on the basis of the result of detection by the heat flux sensor 4.

In the runout detection device 1, the displacement unit 2 is displaced in accordance with runout or a change in runout of the rotating member 100, and the elastic member 3 deforms in accordance with this displacement of the displacement unit 2. Furthermore, in the runout detection device 1, the heat flux sensor 4 detects a change in heat flux due to this deformation of the elastic member 3, and thus it is possible to detect runout or a change in runout of the rotating member 100. In particular, the runout detection device 1 is capable of directly measuring runout of the rotating member 100, that is, displacement of the rotating member 100. This therefore enables the runout detection device 1 to accurately detect runout of the rotating member 100 compared to, for example, the runout correction device disclosed in the published patent document described above.

Furthermore, in the runout device 1, the displacement unit 2 includes a roller portion 2b which rotates following rotation of the rotating member 100 when the roller portion 2b is in contact with the rotating member 100.

Thus, the detection device 1 enables the displacement unit 2 to be displaced without interference with the rotation of the rotating member 100.

Furthermore, the runout detection device 1 includes the abnormality estimation unit 7 which, when the result of detection by the heat flux sensor 4 has a value exceeding the predetermined threshold value t, estimates that the rotating member 100 is abnormally runout.

Thus, the runout detection device 1 enables the abnormality estimation of whether the runout of the rotating member 100 is abnormal to be performed on the basis of the detected runout or change in runout of the rotating member 100.

Second Embodiment

Figure 7:
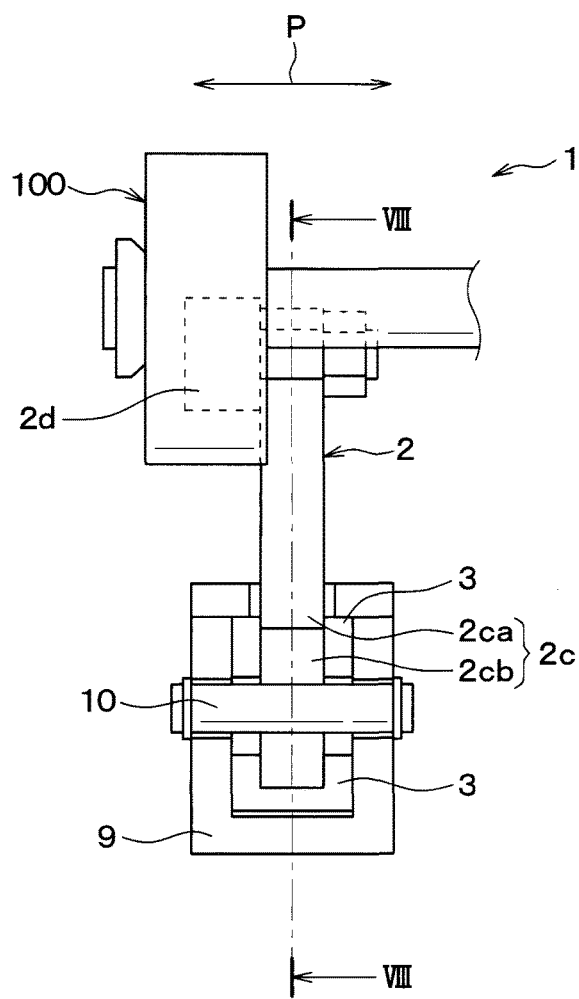
FIG. 7 is a view illustrating an overall configuration in which a runout detection device according to the second embodiment is installed for a rotating member.
Figure 8:
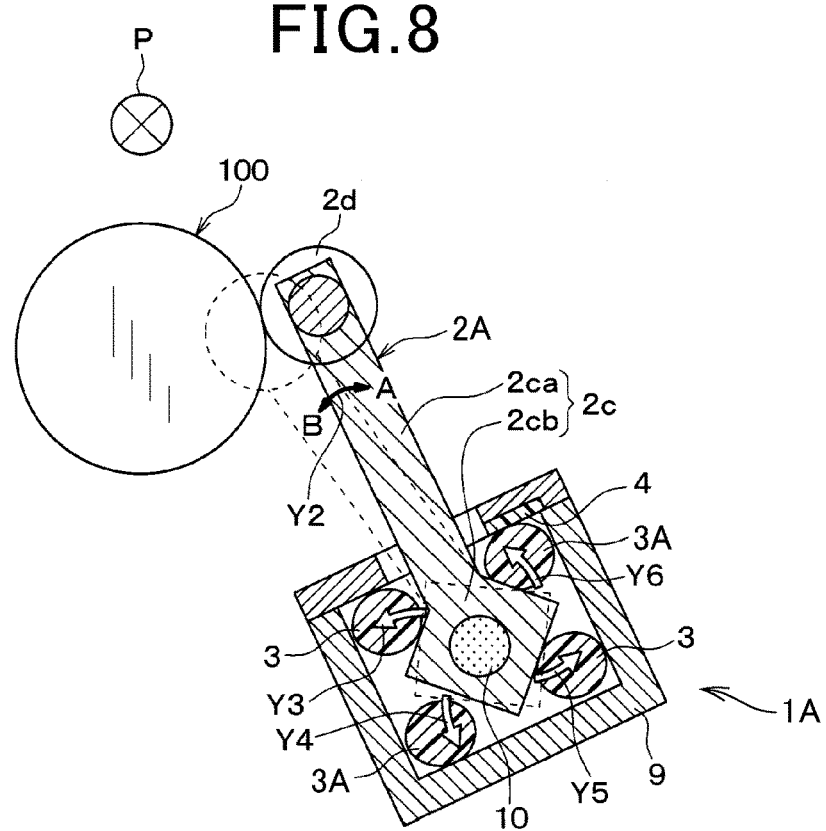
FIG. 8 is a view illustrating a configuration of the runout detection device illustrated in FIG. 7, at a cross-section taken along line VIII-VIII of FIG. 7.

The second embodiment of the present disclosure will be described with reference to FIG. 7 and FIG. 8. Compared to the first embodiment, the present embodiment is different in the configurations, etc., of the displacement unit 2 and the elastic member 3. The other points are basically the same as those in the first embodiment and as such, only the points different from the first embodiment will be explained. Note that in FIG. 7 and FIG. 8, illustrations of the abnormality estimation unit 7 and the display unit 8 are omitted. The arrows denoted by a reference sign Y2 in FIG. 8 represent the directions in which the displacement unit 2 is displaced when the runout of the rotating member 100 changes from that in the state illustrated in FIG. 8. The arrows denoted by reference signs Y3 to Y6 in FIG. 8 represent the directions in which the elastic member 3 deforms when the runout of the rotating member 100 increases from that in the state illustrated in FIG. 8.

As illustrated in FIG. 7 and FIG. 8, a runout detection device 1A according to the present embodiment includes a displacement unit 2A, elastic members 3A, the heat flux sensor 4, the abnormality estimation unit 7, and the display unit 8. In addition, the runout detection device 1A according to the present embodiment further includes: a casing unit 9 which supports the elastic member 3A; and a support mechanism 10 which causes the casing unit 9 to support the displacement unit 2A.

The displacement unit 2A according to the present embodiment includes a base portion 2c and a roller portion 2d. As illustrated in FIG. 7 and FIG. 8, in the present embodiment, the base portion 2c of the displacement unit 2A includes a rod-shaped portion 2ca and a polyhedron-shaped portion 2cb. The roller portion 2d is formed at a first end of the rod-shaped portion 2ca while the polyhedron-shaped portion 2cb is formed on a second end, which is opposite to the first end, of the rod-shaped portion 2ca. Here, the polyhedron-shaped portion 2cb of the displacement unit 2A is in the form of a quadrangular prism as an example. In the present embodiment, the rod-shaped portion 2ca and the polyhedron-shaped portion 2cb of the displacement unit 2A integrally rotate around the support mechanism 10 to be described later, as a fulcrum point, in accordance with displacement of the rotating member 100. The roller portion 2d is a circular cylindrical rotating member supported by the base portion 2c of the displacement unit 2 while being allowed to rotate independently of rotation of the entire displacement unit 2A. The roller portion 2d rotates following rotation of the rotating member 100 when the roller portion 2d is in contact with the rotating member 100. Note that the rod-shaped portion 2ca of the displacement unit 2A includes a material such as stainless steel, for example. Likewise, the polyhedron-shaped portion 2cb of the displacement unit 2A includes a material such as stainless steel, for example. The roller portion 2d includes a resin such as urethane or Delrin, for example.

As illustrated in FIG. 7 and FIG. 8, in the present embodiment, the elastic members 3A are provided around the polyhedron-shaped portion 2cb. The elastic members 3A are housed in the casing unit 9. Each of the elastic members 3A is disposed close to a corresponding surface among a plurality of surfaces of the polyhedron-shaped portion 2cb. Specifically, each of the elastic members 3A is disposed in a position that allows the elastic member 3A to deform in contact with the corresponding surface of the polyhedron-shaped portion 2cb when the polyhedron-shaped portion 2cb rotates. Here, the elastic members 3A are four circular cylindrical elastic members as an example. Subsequently, in the present embodiment, when the polyhedron-shaped portion 2cb of the displacement unit 2A rotates around the support mechanism 10 as the fulcrum point, pressing force is applied to the side surfaces of the circular cylinders of the four circular cylindrical elastic members 3A as a result of displacement of the surfaces of the polyhedron-shaped portion 2cb along with the rotation. In this way, the four circular cylindrical elastic members 3A are pressed and compressed. As described above, in the present embodiment, each of the elastic members 3A is in the shape of a circular cylinder, and the side surface of the circular cylinder, which is a curved surface, is pressed by the polyhedron-shaped portion 2cb (that is, the displacement unit 2A). Therefore, in the present embodiment, the pressing force due to the displacement unit 2A can be uniformly and stably applied to each of the elastic members 3A.

Next, an operation of the runout detection device 1A according to the present embodiment will be described.

As illustrated in FIG. 7 and FIG. 8, the runout detection device 1A is disposed in a predetermined position, and the rotating member 100 is brought into contact with the displacement unit 2A of the runout detection device 1A. At this time, in the present embodiment, the displacement unit 2A of the runout detection device 1A is in contact with each of the elastic members 3A to the extent that the elastic member 3A is slightly compressed. This is the state of the runout detection device 1A at the start of measurement in the present embodiment.

At the start of measurement, first, each elastic member 3A is slightly compressed as described above, and therefore, electromotive force generated in the heat flux sensor 4 is substantially zero.

When the rotating member 100 is largely deviated after the start of measurement, the displacement unit 2A rotates around the support mechanism 10 as the fulcrum point in the direction denoted by a reference sign A or B as viewed in FIG. 8. For example, in the case of rotation in the direction denoted by the reference sign A, each elastic member 3A is more compressed than that at the start of measurement. Accordingly, electromotive force corresponding to the degree of a change in runout of the rotating member 100 is generated in the heat flux sensor 4, and is detected by the abnormality estimation unit 7 as runout of the rotating member 100, specifically, runout that causes the rotating member 100 to be displaced toward the displacement unit 2A.

When there occurs runout that causes the rotating member 100 to be displaced away from the displacement unit 2A, the displacement unit 2A rotates around the support mechanism 10, as the fulcrum point, in the direction denoted by the reference sign B as viewed in FIG. 8. This releases the compression of each elastic member 3A, allowing the elastic member 3A to be restored by elastic deformation. This results in cold energy being generated inside of each elastic member 3A. Accordingly, the temperature of the front side of the heat flux sensor 4 is reduced and as a result, the difference in temperature between the front side and the back side of the heat flux sensor 4 is different from that before the runout of the rotating member 100 is reduced. This leads to a change in the electromotive force that is generated in the heat flux sensor 4, and the abnormality estimation unit 7 detects this change as runout that causes the rotating member 100 to be displaced away from the displacement unit 2A. Note that in the case where the difference in temperature between the front side and the back side of the heat flux sensor 4 is reversed in sign between before and after displacement of the rotating member 100, the sign of the value of the electromotive force is also reversed.

In the runout detection device 1A, similar to the first embodiment, it is possible to detect runout or a change in runout of the rotating member 100, and the abnormality estimation of whether or not the runout of the rotating member 100 is abnormal can be performed on the basis of the detected runout or change in runout of the rotating member 100.

Furthermore, in the runout detection device 1A according to the present embodiment, it is possible to efficiently deform each of the elastic members 3A using a corresponding one of the surfaces of the polyhedron-shaped portion 2cb, and thus it is possible to efficiently increase the electromotive force in the heat flux sensor 4.

Third Embodiment

Figure 9:
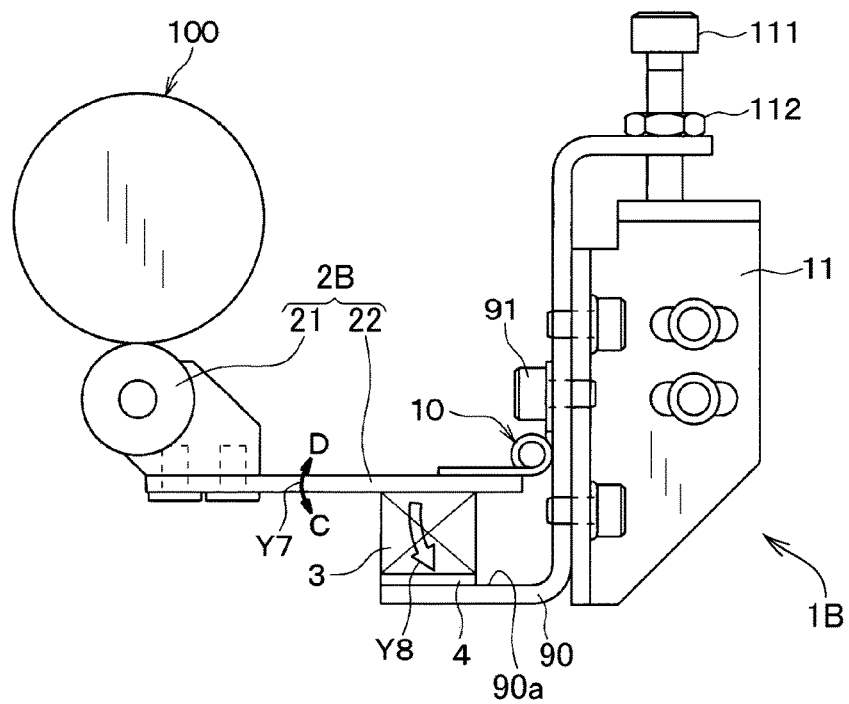
FIG. 9 is a view illustrating an overall configuration in which a runout detection device according to the third embodiment which is installed for a rotating member.

The third embodiment of the present disclosure will be described with reference to FIG. 9. The basic configuration and function of a runout detection device 1B according to the present embodiment are substantially the same as those of the runout detection devices 1 and 1A according to the first and second embodiments. Note that in FIG. 9, illustrations of the abnormality estimation unit 7 and the display unit 8 are omitted. The arrows denoted by a reference sign Y7 in FIG. 9 represent the directions in which a displacement unit 2B is displaced when the runout of the rotating member 100 changes from that in the state illustrated in FIG. 9. The arrow denoted by a reference sign Y9 in FIG. 9 represents the direction in which the elastic member 3 deforms when the runout of the rotating member 100 increases from that in the state illustrated in FIG. 9.

As illustrated in FIG. 9, the runout detection device 1B according to the present embodiment includes the displacement unit 2B, the elastic member 3, the heat flux sensor 4, the abnormality estimation unit 7, and the display unit 8. The runout detection device 1B further includes: a casing unit 90 which supports the elastic member 3; the support mechanism 10 which causes the casing unit 90 to support the displacement unit 2B; and an adjustment support member 11 for supporting the casing unit 90 and adjusting the position of the casing unit 90.

The displacement unit 2B according to the present embodiment includes a base portion 20 and roller portions 21. As illustrated in FIG. 9, in the present embodiment, the base portion 20 of the displacement unit 2B includes a rod-shaped member. The roller portions 21 are formed at an end of the base portion 20. The roller portion 21 is a circular cylindrical rotating member supported by the base portion 20 while being allowed to rotate independently of rotation of the entire displacement unit 2B. The roller portion 21 rotates following rotation of the rotating member 100 when the roller portion 21 is in contact with the rotating member 100. Note that the base portion 20 includes a material such as stainless steel, for example. Likewise, the roller portion 21 includes a resin such as urethane or Delrin, for example.

As illustrated in FIG. 9, in the present embodiment, the elastic member 3 is disposed between the base portion 20 of the displacement unit 2B and a surface 90a of the casing unit 90 which is oriented toward the displacement unit 2B. Specifically, the elastic member 3 is disposed so as to abut on both of the base portion 20 of the displacement unit 2B and the heat flux sensor 4 disposed on the surface 90a of the casing unit 90.

As illustrated in FIG. 9, the support mechanism 10 rotatably supports the displacement unit 2B. Specifically, the support mechanism 10 according to the present embodiment is a typical hinge including two blade-like portions and a rotation support portion which supports the two blade-like portions so that the two blade-like portions are rotatable relative to each other. In the present embodiment, one of the two blade-like portions is secured to the casing unit 90 by a screw 91, and the other is secured to the base portion 20 of the displacement unit 2B with adhesive. In the present embodiment, the support mechanism 10 having such a configuration enables rotation of the base portion 20 of the displacement unit 2B.

The adjustment support member 11 supports the casing unit 90. As illustrated in FIG. 9, the adjustment support member 11 includes: a protrusion portion 111 which is inserted into a hole formed in the casing unit 90; and a nut 112 for securing the protrusion portion 111 to the casing unit 90. Specifically, the protrusion portion 111 of the adjustment support member 11 is secured to the casing unit 90 by the nut 112, and thus the casing unit 90 is secured by the adjustment support member 11. In the present embodiment, it is possible to adjust the position of the casing unit 90 relative to the adjustment support member 11 by adjusting the securement position of the nut 112 relative to the protrusion portion 111. Specifically, the vertical position of the casing unit 90 as viewed in FIG. 9 can be adjusted.

Next, an operation of the runout detection device 1B according to the present embodiment will be described.

As illustrated in FIG. 9, the runout detection device 1B is disposed in a predetermined position, and the rotating member 100 abuts on the displacement unit 2B of the runout detection device 1B. At this time, in the present embodiment, the displacement unit 2B of the runout detection device 1B is in contact with the elastic member 3 to the extent that the elastic member 3 is slightly compressed. This is the state of the runout detection device 1B at the start of measurement in the present embodiment.

At the start of measurement, first, the elastic member 3 is slightly compressed as described above, and therefore, electromotive force generated in the heat flux sensor 4 is substantially zero.

When the rotating member 100 is largely deviated after the start of measurement, the displacement unit 2B rotates around the support mechanism 10, as a fulcrum point, in the direction denoted by a reference sign C or D as viewed in FIG. 9. For example, in the case of rotation in the direction denoted by the reference sign C, the elastic member 3 is more compressed than that at the start of measurement. Accordingly, electromotive force corresponding to the degree of a change in runout of the rotating member 100 is generated in the heat flux sensor 4, and is detected by the abnormality estimation unit 7 as runout of the rotating member 100, specifically, runout that causes the rotating member 100 to be displaced toward the displacement unit 2B.

When there occurs runout that causes the rotating member 100 to be displaced away from the displacement unit 2B, the displacement unit 2B rotates around the support mechanism 10, as the fulcrum point, in the direction denoted by the reference sign D as viewed in FIG. 9. This releases the compression of the elastic member 3, allowing the elastic member 3 to be restored by elastic deformation, which results in cold energy being generated inside of the elastic member 3. Accordingly, the temperature of the front side of the heat flux sensor 4 is reduced and as a result, the difference in temperature between the front side and the back side of the heat flux sensor 4 is different from that before the runout of the rotating member 100) is reduced. This leads to a change in the electromotive force that is generated in the heat flux sensor 4, and the abnormality estimation unit 7 detects this change as runout that causes the rotating member 100 to be displaced away from the displacement unit 2B. Note that in the case where the difference in temperature between the front side and the back side of the heat flux sensor 4 is reversed in sign between before and after displacement of the rotating member 100, the sign of the value of the electromotive force is also reversed.

In the present runout detection device 1B, similar to the first and second embodiments, it is possible to detect runout or a change in runout of the rotating member 100, and the abnormality estimation of whether or not the runout of the rotating member 100 is abnormal can be performed on the basis of the detected runout or change in runout of the rotating member 100.

Fourth Embodiment

Figure 10:
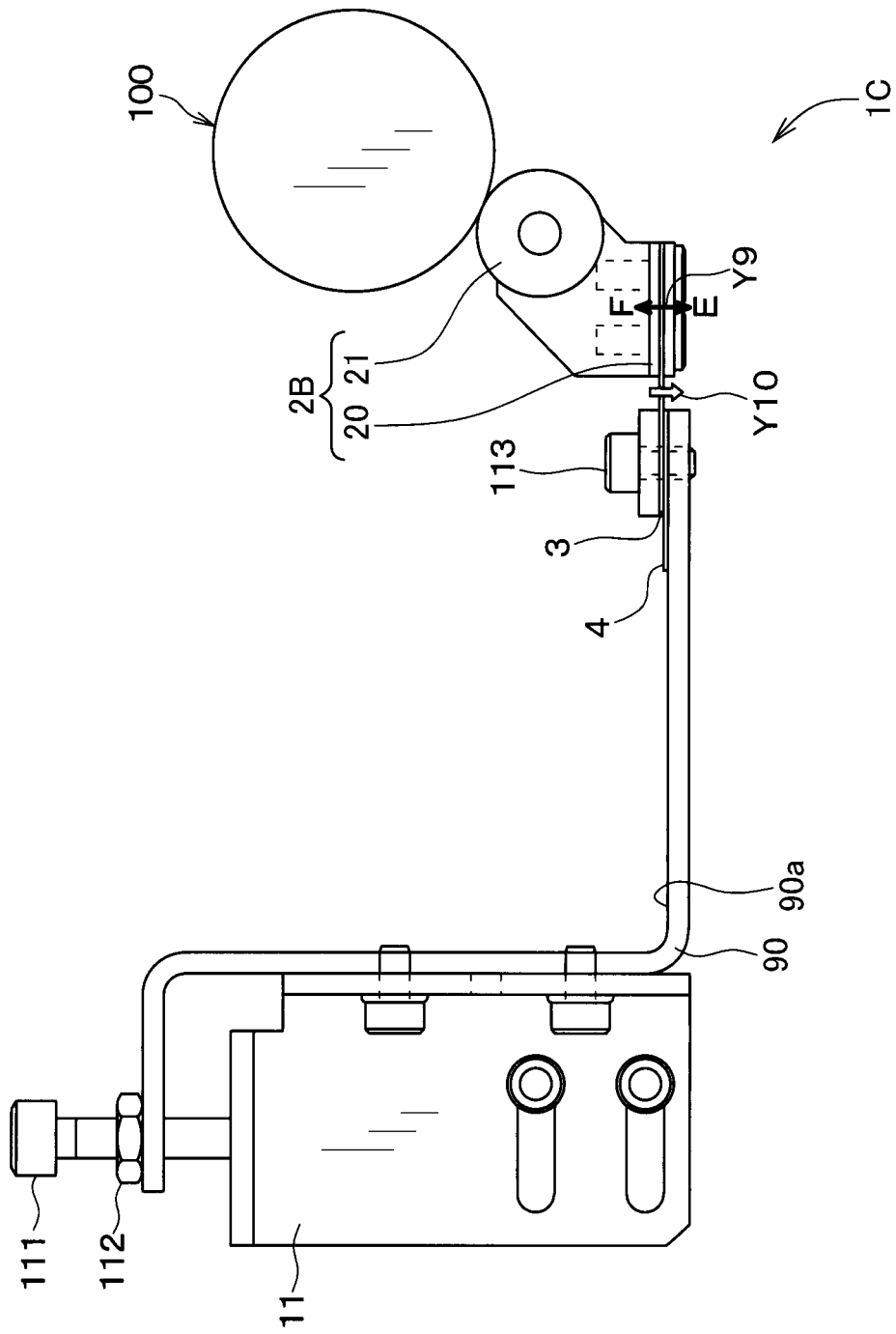
FIG. 10 is a view illustrating an overall configuration in which a runout detection device according to the fourth embodiment is installed for a rotating member.
Figure 11:
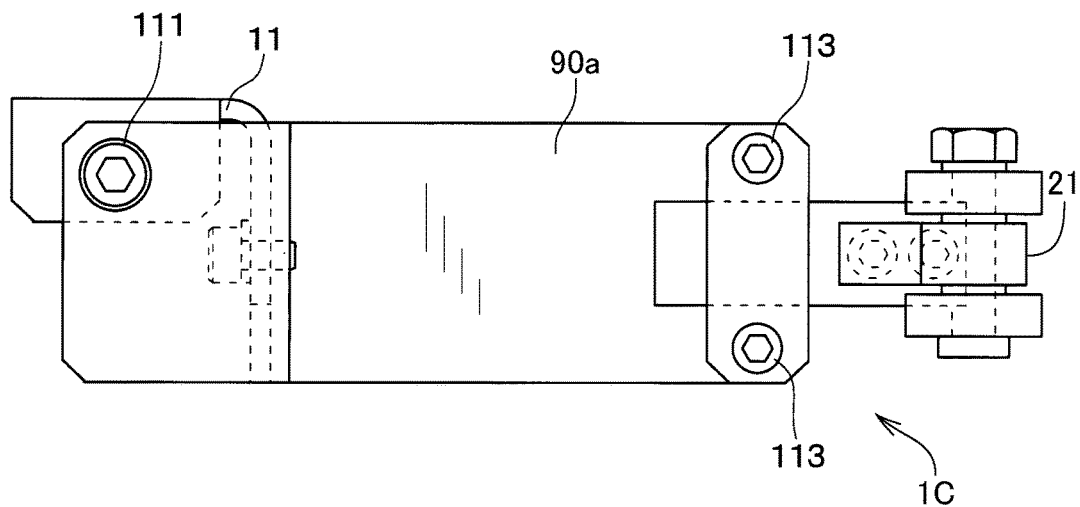
FIG. 11 is a bottom view of the runout detection device illustrated in FIG. 10.
Figure 12:
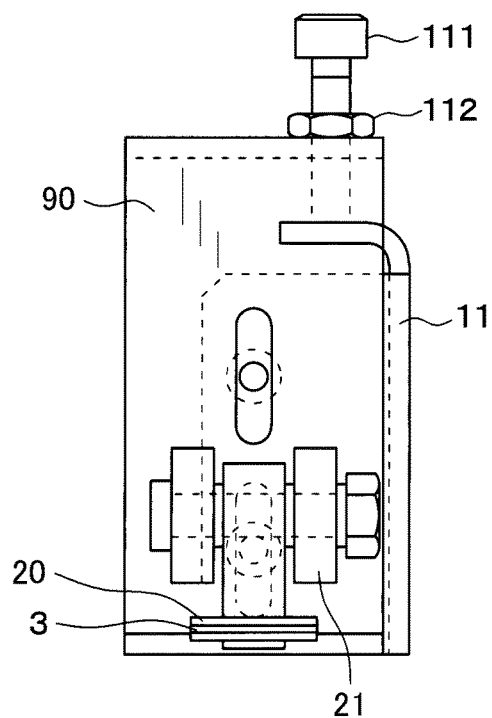
FIG. 12 is a side view of the runout detection device illustrated in FIG. 10.

The fourth embodiment of the present disclosure will be described with reference to FIG. 10 to FIG. 13. The basic configuration and function of a runout detection device 1C according to the present embodiment are substantially the same as those of the runout detection device B according to the third embodiment. Note that in FIG. 10 to FIG. 13, illustrations of the abnormality estimation unit 7 and the display unit 8 are omitted. The arrows denoted by a reference sign Y9 in FIG. 10 represent the directions in which the displacement unit 2B is displaced when the runout of the rotating member 10) changes from that in the state illustrated in FIG. 10. The arrow denoted by a reference sign Y10 in FIG. 10 represents the direction in which the elastic member 3 deforms *when the runout of the rotating member 100 increases in the direction denoted by a reference sign E from that in the state illustrated in FIG. 10. Furthermore, in FIG. 11 and FIG. 12, an illustration of the rotating member 100 is omitted.

As illustrated in FIG. 10, in the present embodiment, the elastic boy 3 which elastically deforms in accordance with displacement of the displacement unit 2B includes a metal plate.

As illustrated in FIG. 10, in the present embodiment, the elastic member 3 including the metal plate is secured to the casing unit 90 by screws 113 at one end in a direction perpendicular to the thickness direction of the metal plate (that is, in the horizontal direction as viewed in FIG. 10). The heat flux sensor 4 is disposed between the one end of the metal plate and the screws 113 so as to be in contact with the one end of the metal plate.

Furthermore, as illustrated in FIG. 10, in the present embodiment, the elastic member 3 including the metal plate is secured to the base portion 21 of the displacement unit 2B at the other end in the direction perpendicular to the thickness direction of the metal plate.

Note that the present embodiment eliminates the support mechanism 10 and the screw 91.

Next, an operation of the runout detection device 1C according to the present embodiment will be described.

As illustrated in FIG. 10, the runout detection device 1C is disposed in a predetermined position, and the rotating member 100 abuts on the displacement unit 2B of the runout detection device 1C. This is the state of the runout detection device 1C at the start of measurement in the present embodiment.

Figure 13:
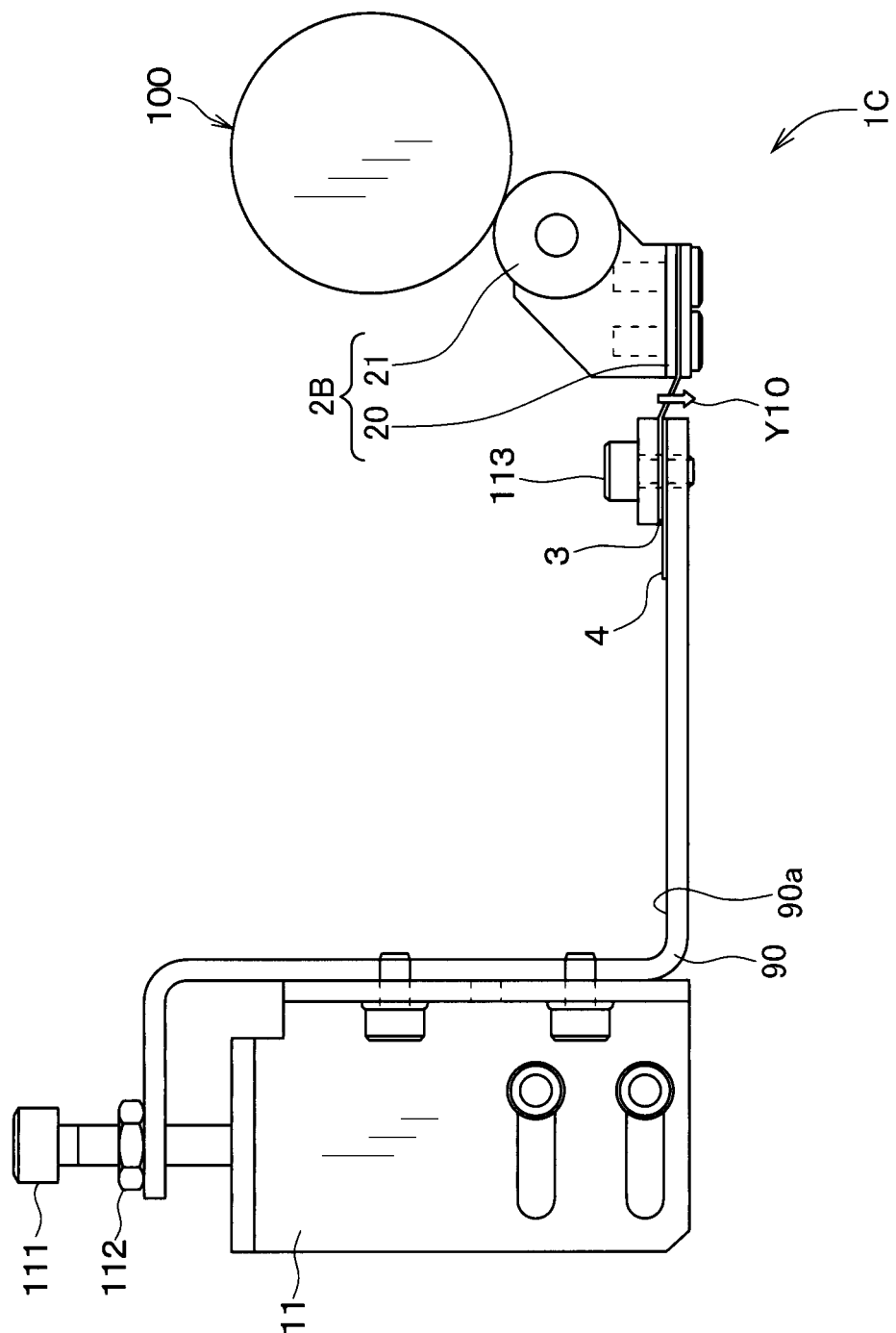
FIG. 13 is another view illustrating the overall configuration for the runout detection device illustrated in FIG. 10.

When the rotating member 100 is largely deviated after the start of measurement, the displacement unit 2B is displaced in the direction denoted by the reference sign E or F as viewed in FIG. 10. For example, in the case of displacement in the direction denoted by the reference sign E, the elastic member 3 is more bent than that at the start of measurement, as illustrated in FIG. 13. Accordingly, electromotive force corresponding to the degree of a change in runout of the rotating member 100 is generated in the heat flux sensor 4, and is detected by the abnormality estimation unit 7 as runout of the rotating member 100.

When there occurs runout that causes the rotating member 100 to be displaced so that the displacement unit 2B returns to the position at the start of measurement, that is, when the displacement unit 2B is displaced in the direction denoted by the reference sign F as viewed in FIG. 10, the compression of the elastic member 3 is released, allowing the elastic member 3 to be restored by elastic deformation, which results in cold energy being generated inside of the elastic member 3. Accordingly, the temperature of the front side of the heat flux sensor 4 is reduced and as a result, the difference in temperature between the front side and the back side of the heat flux sensor 4 is different from that before the runout of the rotating member 100 is reduced. This leads to a change in the electromotive force that is generated in the heat flux sensor 4, and the abnormality estimation unit 7 detects this change as runout that causes the rotating member 100 to be displaced in the direction opposite to the direction of the earlier runout. Note that in the case where the difference in temperature between the front side and the back side of the heat flux sensor 4 is reversed in sign between before and after displacement of the rotating member 100, the sign of the value of the electromotive force is also reversed.

In the present runout detection device 1C, similar to the first to third embodiments, it is possible to detect runout or a change in runout of the rotating member 100, and the abnormality estimation of whether or not the runout of the rotating member 100 is abnormal can be performed on the basis of the detected runout or change in runout of the rotating member 100.

Other Embodiments

The present disclosure is not limited to the embodiments described above, and changes can be made to the present disclosure as appropriate within the range recited in the claims.

For example, each of the displacement units 2 to 2C is configured to include the roller portion 2b or 21 in the corresponding embodiment. Each of the first to fourth embodiments, however, may be designed so that the roller portion 2b or 21 is not provided in the displacement unit 2, 2A, or 2B, and the rotating member 100 abuts on the base portion 2a of the displacement unit 2, 2A, or 2B. In this modification, a surface of the base portion 2a of the displacement unit 2, 2A, or 2B with which the rotating member 100 is brought into contact is preferably configured to have a low coefficient of friction such that the rotating member 100 can easily slide.

In the first aspect disclosed in part or all of the embodiments described above, a runout detection device which detects runout of a rotating member during rotation includes a displacement unit, an elastic member, and a heat flux sensor. The displacement unit is brought into contact with the rotating member and is displaced in accordance with displacement of the rotating member when the displacement unit is in contact with the rotating member. The elastic member elastically deforms in accordance with displacement of the displacement unit. The heat flux sensor detects a heat flux generated by elastic deformation of the elastic member. This runout detection device detects runout of the rotating member on the basis of the result of detection by the heat flux sensor.

In the second aspect disclosed in part or all of the embodiments described above, furthermore in the runout detection device according to the first aspect, the displacement unit includes a roller portion which rotates following rotation of the rotating member when the roller portion is in contact with the rotating member.

Thus, in this runout detection device, the displacement unit can be displaced without interference with the rotation of the rotating member.

In the third aspect disclosed in part or all of the embodiments described above, the runout detection device according to the first or second aspect further includes an abnormality estimation unit which, when the result of detection by the heat flux sensor has a value exceeding a predetermined threshold value, estimates that the rotating member is abnormally run out.

Thus, in this runout detection device, the abnormality estimation of whether or not the runout of the rotating member is abnormal can be performed on the basis of the detected runout or change in runout of the rotating member.

What is claimed is:

1. A runout detection device for detecting runout of a rotating member, the runout detection device comprising:
    a displacement unit that abuts on the rotating member, and is displaced in accordance with displacement of the rotating member while the rotating member abuts on the displacement unit;
    an elastic member that elastically deforms in accordance with displacement of the displacement unit;
    a heat flux sensor that detects a heat flux generated by elastic deformation of the elastic member; and
    a heat conducting member disposed adjacently to the heat flux sensor, so that the heat flux sensor is disposed between the elastic member and the heat conducting member, wherein
    the runout detection device being configured to detect runout of the rotating member based on the heat flux detected by the heat flux sensor.

2. The runout detection device according to claim 1, wherein:
    the displacement unit includes a roller portion that rotates following rotation of the rotating member while the roller portion abuts on the rotating member.

3. The runout detection device according to claim 2, wherein:
    the displacement unit includes a base portion,
    the base portion including:
        a rod-shaped portion having opposing first and second ends, the roller portion is formed at the first end of the rod-shaped portion; and
        a polyhedron-shaped portion formed on the second end, the polyhedron-shaped portion having a plurality of surfaces;
    the elastic member comprising a plurality of elastic members, each of the elastic members being disposed close to a corresponding one of the plurality of surfaces of the polyhedron-shaped portion,
    each of the elastic members being disposed in a position that allows the corresponding elastic member to deform in contact with the corresponding one of the plurality of surfaces of the polyhedron-shaped portion when the polyhedron-shaped portion rotates based on rotation of the roller portion,
    the heat flux sensor being configured to detect the heat flux generated by elastic deformation of each of the plurality of elastic members.

4. The runout detection device according to claim 2, wherein:
    the displacement unit includes a rod-shaped base portion having opposing first and second ends, the roller portion is formed at the first end of the rod-shaped base portion, the runout detection device further comprising:
    a support mechanism configured to rotatably support the rod-shaped base portion,
    the elastic member being disposed to abut on the rod-shaped base portion; and
    wherein:
    rotation of the rotating member rotates the roller portion, so that the rod-shaped base portion is rotated by the support mechanism to cause the elastic member to deform; and
    the heat flux sensor is configured to detect the heat flux generated by elastic deformation of the elastic member.

5. The runout detection device according to claim 1, further comprising:
    an abnormality determining unit configured to determine whether the rotating member is abnormally run out in accordance with a value of the heat flux detected by the heat flux sensor.

6. The runout detection device according to claim 5, wherein:
    the abnormality determining unit is configured to, when it is determined that the value of the heat flux detected by the heat flux sensor exceeds a predetermined threshold value, determine that the rotating member is abnormally run out.

* * * * *